United States Patent [19]

Wood et al.

[11] Patent Number: 4,650,755

[45] Date of Patent: * Mar. 17, 1987

[54] IMMOBILIZING MICROBIAL CELLS WITH POLYFUNCTIONAL AZIRIDINES

[75] Inventors: Louis L. Wood, Rockville; Gary J. Calton, Elkridge, both of Md.

[73] Assignee: Purification Engineering, Inc., Columbia, Md.

[*] Notice: The portion of the term of this patent subsequent to Mar. 13, 2001 has been disclaimed.

[21] Appl. No.: 640,774

[22] Filed: Aug. 14, 1984

Related U.S. Application Data

[63] Continuation-in-part of Ser. No. 465,551, Feb. 10, 1983, and Ser. No. 518,756, Jul. 29, 1983, Pat. No. 4,600,692, each is a continuation-in-part of Ser. No. 358,784, Mar. 16, 1982, Pat. No. 4,436,813.

[51] Int. Cl.$^4$ .................. C12P 37/00; C12P 33/00; C12N 11/08; C12N 11/04

[52] U.S. Cl. .................................... 435/43; 435/52; 435/94; 435/108; 435/109; 435/116; 435/180; 435/182

[58] Field of Search .............. 435/43, 52, 94, 109, 435/108, 116, 178, 179, 180, 181, 182

[56] References Cited

PUBLICATIONS

Porath et al., Methods in Enzymology, vol. XLIV, 1976, pp. 19–45.
Chibata, I., Immobilized Enzymes, John Wiley & Sons, N.Y., 1978, pp. 14–27, 50–55 & 72–81.

*Primary Examiner*—David M. Naff
*Attorney, Agent, or Firm*—Cushman, Darby & Cushman

[57] ABSTRACT

Microbial cells are immobilized with a curable polyaziridine or polyfunctional aziridine prepolymer to obtain an insoluble, crosslinked polymer containing the cells. The microbial cells immobilized may be cells having L-aspartase or L-phenylalanine transaminase activity for the production of L-aspartic acid or L-phenylalanine. The polymer containing the cells may be formed as a coating on a solid inert carrier.

27 Claims, No Drawings

IMMOBILIZING MICROBIAL CELLS WITH POLYFUNCTIONAL AZIRIDINES

RELATED APPLICATIONS

The present application is a continuation-in-part of pending application Ser. No. 465,551, filed Feb. 10, 1983 and application Ser. No. 518,756, filed July 29, 1983, now U.S. Pat. No. 4,600,692, both of said earlier applications being continuations-in-part of application Ser. No. 358,784, filed Mar. 16, 1982, now U.S. Pat. No. 4,436,813. The subject matter of said earlier applications is incorporated herein by reference.

The present invention is concerned with the immobilization of microbial cells and processes for preparing and using the same. The invention is particularly concerned with an improved process for manufacturing L-aspartic acid and L-phenylalanine using immobilized microbial cells, notably *E. coli* cells, which contain L-aspartase activity and L-phenylalanine transaminase activity. However, the immobilization and use of other cells are also contemplated.

BACKGROUND TO THE INVENTION

There is a considerable amount of prior art regarding the immobilization of *E. coli* or other microbial cells for use in the preparation of L-aspartic acid. For example, U.S. Pat. No. 3,791,926 (Chibata et al) describes a process for the production of L-aspartic acid which involves polymerizing a monomer selected from acrylamide, N,N'-lower alkylene-bis(acrylamide) and bis(acrylamidomethyl) either in an aqueous suspension containing an aspartase-producing microorganism such as *E. coli* ATCC no. 11303. The resultant immobilized aspartase-producing microorganism is treated with ammonium fumarate or a mixture of fumaric acid or its salt and an inorganic ammonium salt which by enzymatic reaction gives L-aspartic acid.

The immobilization of *E. coli* cells containing aspartase activity and use of the resulting immobilized cells for the production of L-aspartic acid are also described by Fusee et al, *Applied and Environmental Microbiology*, Vol. 42, No. 4, pages 672-676 (October 1981). According to Fusee et al, the cells are immobilized by mixing a suspension of the cells with a liquid isocyanate-capped polyurethane prepolymer (HYPOL®) so as to form a "foam" containing the immobilized cells.

Sato et al (*Biochimica et Biophysica Acta*, 570 (1979) pages 179–186) have disclosed the immobilization of *E. coli* cells containing aspartase activity with K-carrageenan, and use of the immobilized preparation for the production of L-aspartic acid.

Additional literature disclosures describing the immobilization of microbial cells in urethane prepolymers or polyurethanes or the like include the following:

(a) Immobilization of Microbial Cells in Polyurethane Matrices, by Klein et al, *Biotechnology Letters*, Vol. 3, No. 2, pages 65-70 (1981)

(b) Hyrophilic Urethane Prepolymers: Convenient Materials for Enzyme Entrapment, *Biotechnology and Bioengineering*, Vol. XX, pages 1465-1469 (1978);

(c) Transformation of Steroids by Gel-Entrapped Cells in Organic Solvent, by Omata et al, *European J. Applied Microbiology and Biotechnology*, 8, pages 143-155 (1979); and (d) Entrapment of Microbial Cells and Organelles With Hydrophilic Urethane Prepolymers, by Tanaka et al, *European J. Applied Microbiology and Biotechnology*, 7, 351-354 (1979).

The above noted processes for preparing L-aspartic acid using immobilized microbial cells suffer from various disadvantages. For example, K-carrageenan gum and polyurethane "foam" as disclosed by Fusee et al and Sato et al are relatively soft and compressible. Hence when these immobilized cell compositions are used, in a column through which ammonium fumarate is passed for conversion to ammonium aspartase, they tend to be compressed and plug up, particularly where high flow rates and/or relatively tall column heights are involved.

OBJECTS OF THE INVENTION

One main object of the present invention is to provide an improved process for preparing L-aspartic acid using L-aspartase active microbial cells, preferably *E. coli* cells, which have been immobilized in a special way whereby the resulting composition is highly effective for the preparation of L-aspartic acid batchwise or in continuous fashion.

Another main object of the present invention is to provide an improved proces for preparing L-phenylalanine using L-phenylalanine transaminase active microbial cells, such as *E. coli* cells, which have been immobilized in a special way whereby the resulting composition is highly effective for the preparation of L-phenylalanine batchwise or in continuous fashion.

More specific objects include:

The provision of an improved process for preparing L-aspartic acid from ammonium fumarate using immobilized *E. coli* cells which maintain optimum L-aspartic activity for relatively long periods of time.

The provision of an improved process for preparing L-phenylalanine from L-aspartic acid plus phenylpyruvate using immobilized *E. coli* cells which maintain optimum L-phenylalanine transaminase activity for relatively long periods of time.

Other specific objects of the invention are to provide novel immobilized microbial systems suitable for use in making L-aspartic acid and L-phenylalanine which obviate problems encountered in prior procedures involving the use of immobilized cells. Other objects will also be hereinafter apparent.

SUMMARY OF INVENTION

According to one aspect of the invention, there is provided a process for preparing L-aspartic acid by contacting ammonium fumarate or its equivalent with an immobilized microbial cell composition comprising *E. coli* ATCC 11303 cells or equivalent cells containing L-aspartase activity, the cells being immobilized by means of a fixed, insoluble, crosslinked polymer obtained by curing a curable prepolymer material selected from the group consisting of polyaziridine prepolymers cured at a temperature below the temperature at which the L-aspartase activity of the microbial cells is significantly reduced. Advantageously the cell/cross-linked polymer composition as used constitutes a coating on a solid inert carrier although this is not essential. However, the application of the immobilized cell/cross-linked polymer coating on the carrier provides a highly advantageous form of the cell/polymer composition for use in preparing L-aspartic acid.

According to another aspect of the invention, there is provided a process for preparing L-phenylalanine by contacting soluble L-aspartic acid salts with soluble salts of phenylpyruvic acid in the presence of an immobilized microbial cell composition comprising E. coli ATCC 11303 cells or equivalent cells containing L-phenylalanine transaminase activity, the cells being immobilized by means of a fixed, insoluble, crosslinked prepolymer obtained by curing a curable prepolymer material selected from the group of polyfunctional aziridine prepolymers cured at a temperature below the temperature at which the L-phenylalanine transaminase activity of the microbial cells is significantly reduced. Here again the cell/crosslinked polymer composition is advantageously, although not necessarily, used as a coating on a solid inert carrier.

It is also a feature of this invention that, though not limited to polyfunctional aziridine methods of immobilization, since both L-aspartase and L-phenylalanine transaminase are present on the same microbe cell, it is possible to prepare L-phenylalanine starting with ammonium fumarate plus soluble phenylpyruvate salts with these immobilized cell compositions.

The preferred aspects of the invention contemplate the provisions of immobilized E. coli cells having L-aspartase and/or L-phenylalanine transaminase activities, the cells being immobilized by means of a crosslinked, water-insoluble polymer obtained by curing a polyaziridine prepolymer.

Broadly speaking, the invention is dependent on binding whole or ruptured cells of E. coli, notably E. coli ATCC 11303, or the equivalent, which are known to have L-aspartase and L-phenylalanine transaminase activities and therefore are capable of producing L-aspartic acid (or ammonium salt thereof) and L-phenylalanine by conversion of ammonium fumarate, or phenylpyruvate plus a suitable L-amino acid, respectively, in a novel and useful configuration using a special crosslinked polymer system as set forth above to bind the cells.

The polyaziridine prepolymer system can be crosslinked at temperature below 40° C. and in the presence of relatively large volumes of water containing E. coli cells while still maintaining useful L-aspartase and L-phenylalanine transaminase activities of the cells. It is a surprising aspect of the invention that such aqueous crosslinking conditions leave the E. coli cells with their L-aspartase and L-phenylalanine transaminase activities even though the cells are immobilized in insoluble, crosslinked polymer networks.

Another unique aspect of the invention is that the wet dispersion of the E. coli cells in the aqueous polymer solutions can be taken to dryness while the immobilized cells still surprisingly retain much of their original L-aspartase and phenylalanine transaminase activities. The drying process has the advantage of providing strong, well-crosslinked, insoluble compositions in the form of coatings, membranes, particles, etc. having high concentrations of cells retaining the desired enzyme activities.

The novel immobilized L-aspartase cell compositions disclosed herein have been found to outperform the immobilized L-aspartase active E. coli cell compositions previously reported by, for example, Fusee et al and Sato et al in the references noted above.

The polyfunctional aziridine prepolymer systems suitable for use to provide the crosslinked polymer networks for immobilizing cells according to this invention are initially mobile, soluble non-crosslinked compounds having on the average greater than two aziridine groups attached to the molecule. For the purposes of this invention, the methods of preparing polyfunctional aziridine compounds are essentially, if not completely, similar to the methods outlined in "Encyclopedia of Polymer Science and Technology" Vol. 1, p. 735-736 (1964, J. Wiley & Sons) and in "Heterocyclic Compounds with Three and Four-Membered Rings" pt. 1, Cpt. 2, p. 542-550 (1964, J. Wiley & Sons):

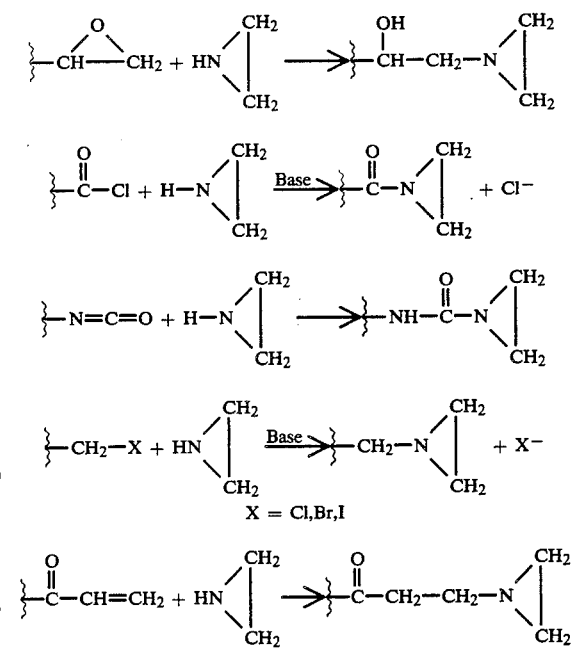

The types of compounds having greater than 2 aziridine groups useful in this invention can range from comparatively small molecules of less than 500 mol. wt. to uncrosslinked polymers having mol. wt. considerably greater than 500. Illustrative, but non-limiting, examples of the smaller class of polyfunctional aziridine are the commercially available XAMA ®-2 and XAMA ®-7 compounds from the Cordova Chemical Company (Michigan):

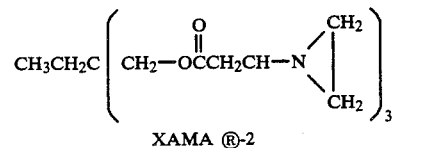

XAMA ®-2
Trimethylolpropane-tris [β-(N—aziridinyl)propionate]

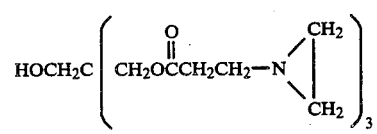

XAMA ®-7
Pentaerythritol-tris-[β-(N—aziridinyl)propionate]

Illustrative, but not limiting examples of the larger polyfunctional aziridine molecules are those described by Jellanek, T., et al, Quimnquenn. Int. Wool Text. Res. Conf., 6th, 1980 [CA 94:85565b]:

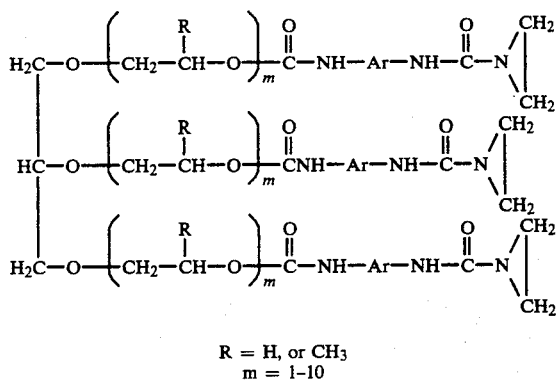

R = H, or CH₃
m = 1-10

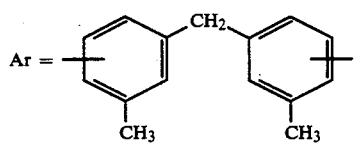

Thus, it can be seen that any suitable, mobile soluble molecules having greater than 2 sites available for attaching aziridine groups by the methods listed above, are useful starting material for the polyfunctional aziridines required for this invention.

The outstanding value in this invention of molecules having on the average greater than 2 aziridine groups is their ability under mild conditions (less than 40° C., pH between 2 and 10) in water to react with themselves and with a wide variety of other functional groups on other molecules or surfaces:

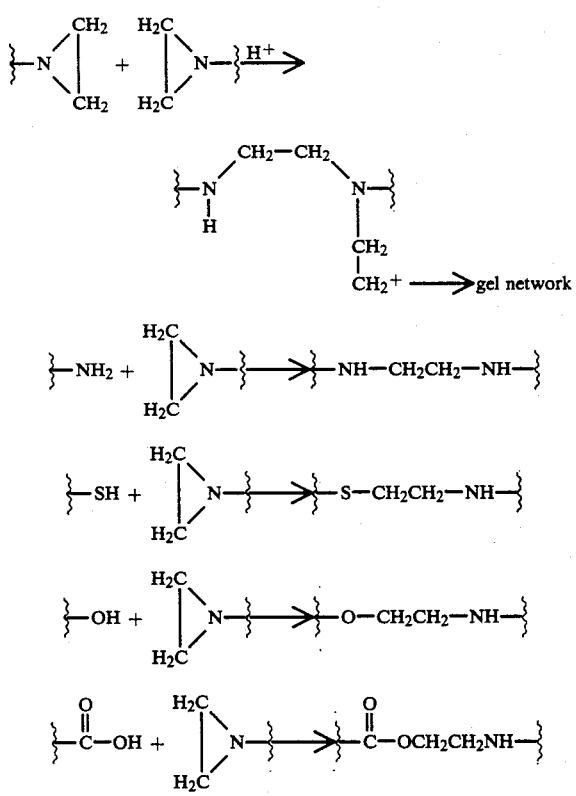

Thus, a wide variety of complex gel networks can be formed containing immobilized whole cells, enzymes, and other important biologically active compounds which still have useful levels of their original biochemical activities. In general, the resultant gel composites have sufficient openness and hydrophilicity to allow free migration of important chemical substrates to interact with all of the immobilized species, and thus permit high levels of useful transformations to take place.

In 1976, J. Porath very briefly suggested that the aziridine groups among others (imido carbonates, carbonates, oxirznes, activated double bonds, activated bologens) might be introduced onto existing solid supports for attachment to enzymes ("Methods for Enzymology", Vol. 44, p. 26). There was no further discussion of how aziridines were to be introduced. However, from an examination of Porath's work, especially with his extensive investigations of oxiranes (the oxygen analogs of aziridines) or exactly bisoxiraines, it is evident that Porath contemplated the use of bisazeridines for the attachment of enzyles to solid supports:

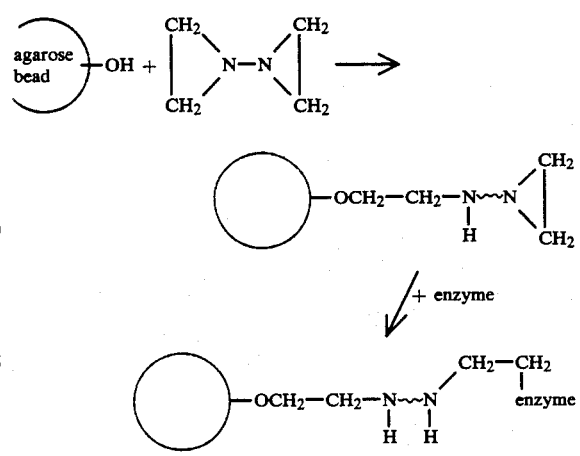

It was not apparently evident at the time that molecules having more than two aziridine groups were capable by themselves to form insoluble solid gels under mild, aqueous conditions while also interacting with functional groups (—NH₂, —SH, —COOH, OH) on cells, enzymes or other biologically active compounds.

Any of the above-noted polyfunctional aziridines having greater than 2 aziridine groups/molecules may be used to immobilize L-aspartase or L-phenylalanine transaminase active E. coli cells, according to the invention, to provide cell/polymer compositions having a variety of different forms and shapes. For example, the immobilized cell/polymer composition may be prepared in the form of membranes, filaments, fibers, tubes, beads or the like. A particularly important embodiment of the invention involves providing the immobilized cell/polymer composition as a coating on an appropriately shaped support which advantageously, although not necessarily, is in the form of solid or reticulated beads or particles composed of an inert solid organic or inorganic, porous or non-porous material. As noted earlier, the composition of the invention can be cured with or without drying with substantively affecting the L-aspartase or L-phenylalanine transaminase activity of the cells and, as a consequence, the composition can be made up in the form of or wet dried coated beads or other particulate material and stored until needed for use. Typically, useful supports or carriers for the immobilized cell/crosslinked polymer compositions of the invention include the following in bead or particle form:
- Molecular sieves
- Ion exchange resins
- Alumina
- Silica and silica gel
- Foraminifera skeletons
- Polymer latexes
- Metals It is a useful property of the polymer systems used in the present invention that they can be contacted or mixed in water with *E. coli* cells containing L-aspartase and/or L-phenylalanine transaminase and then crosslinked (or cured) to form insoluble and relatively fixed polymer matrices which hold or otherwise immobilize the *E. coli* cells. It is particularly useful that the crosslinking conditions which need to be used are mild enough so that the desired enzyme activities of the *E. coli* cells are maintained.

As indicated, a particularly desirable composition according to the invention is obtained by applying the *E. coli* cells containing the desired enzyme activities and the immobilizing polymer as a coating on hard inorganic or organic polymer beads. Using these relatively noncompressible compositions an L-aspartase and/or L-phenylalanine transaminase active catalyst bed capable of high throughput in a fixed bed or fluidized bed is possible. As noted earlier, the L-aspartase active immobilized cell compositions previously described in the literature involving the use of relatively soft, compressible K-carrageenan gum or polyurethane foam are compressible and therefore tend to plug under high flow rates, and/or tall column (bed) heights.

Various methods may be used to immobilize the *E. coli* ATCC 11303 cells, while retaiing their enzyme activities by combination with cured or crosslinked forms of polyfunctional aziridine prepolymers according to the invention. The prefered method used in any specific situation will depend, at least to some extent, on the prepolymer involved.

Thus, *E. coli* ATCC 11303 cells are advantageously mixed with either neat polyfunctional aziridine prepolymers or solutions of the prepolymers so as to obtain a homogeneous mixture. Typically 1.0 to 500 parts/wt of cells per 10 parts/wt of the prepolymer are used with the preferred range being 5-200 parts/wt of cells to 10 parts/wt of prepolymer. The 10 parts/wt prepolymer is often advantageous in solution with 5 to 1000 parts/wt of water. The preferred proportions are in the range of 10 parts/wt prepolymer in 50 to 200 parts/wt of water.

After distributing the resultant homogeneous mixture in the shape of the desired final configuration (membrane, fiber, coating on solid bead, etc.) the composite may be allowed to cure or crosslink to give an insoluble enzyme active composition by the following means:

Removal of part or nearly all of the water at temperatures below 60° C. (usually between 40° C. and 0° C.) and pressures of 760 to 1.0 Torr.

Allowing the composition to stand at temperatures below 60° C. (usually between 40°-0° C.) without removing the water for periods of 0.5 to 50 hours. Compositions cured with the removal of water appear to give insoluble composites somewhat stronger than composites formed without the removal of water.

The above *E. coli*/polyaziridine compositions can be fabricated into membranes, fibers, beads, etc. but a preferred configuration is to use the compositions as coatings onto high surface area particles. Typically the coating on the beads is formulated so that from 1 to 30 parts/wt wet cells are loaded onto 10 parts/wt beads. Preferably, 5 to 15 parts/wt of cells are coated onto 10 parts/wt of beads.

It is to be understood that this invention is not limited to the immobilization of *E. coli* cells or the use of such immobilized cells for the production of L-aspartic acid or L-phenylalanine. Thus, other cells may be immobilized in generally similar fashion using the indicated curable polyfunctional aziridines. Some of the other types of cells that could be immobilized and the function of the resultant composite are (these are understood to be examples and not limiting):

Production of L-alanine via the immobilization of *Pseudomonas dacunhae*, or other microbe high in aspartase-$\beta$-decarboxylase;

Preparation of 6-amino-penicillanic acid via the immobilization of *Bacillus megaterium*, or other microbe high in penicillin acylase;

High fructose corn syrup from immobilized *Arthrobacter species* ATCC 21748, or other microbes high in glucose isomerase, High fructose corn syrup from the glucose isomerase activity of immobilized *Streptomyces phaeochromogenes;* NRRL B3559;

Production of prednisolone from the steriod dehydrogenase activity of immobilized *Arthrobacter simplex;*

Production of L-phenylalanine from the phenylalanine ammonia lyase activity of immobilized *Rhodosporidium toruloides* ATCC 10788.

The immobilized cell/polymer compositions of this invention may be used to make their intended products (for example, L-aspartic acid or L-phenylalanine) by either a batch or continuous process. However, it is noted that these compositions, particularly when coated onto a bead or other particulate support, are especially effective for the continuous conversion of aqueous solutions of substrates to products. Examples are:

Conversion of NH4 fumarate to L-aspartate.

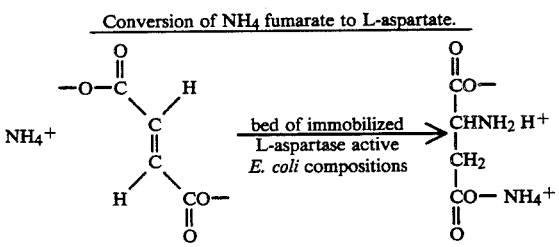

Interaction of L-aspartate with phenylpyruvate to form L-phenylalanine.

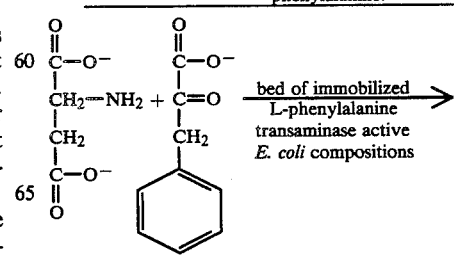

-continued

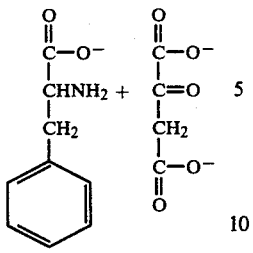

As illustrative of processes which may be used to prepare L-aspartic acid or ammonium L-aspartate according to the invention are the following:
 (i) A batch type process wherein the catalyst compositions are stirred in from 0.1 to 5.0 molar (preferably 0.5 to 2.0 molar) solutions of ammonium fumarate in water at 5.0 to 10.0 pH (preferably 7.5 to 9.5 pH) for periods of 1.0 to 100 hours (preferably 8 to 48 hours) at temperatures below 60° C. (preferably 20° to 45° C.). Broadly from 0.05 to 50 g of immobilized cells, preferably from 1.0 to 15 g, are used per 1.0 mole of starting ammonium fumarate. After the conversion, the catalyst compositions may be removed by filtration or the equivalent for reuse in converting fresh batches of fumarate solutions. The product solutions are obtained in a form suitable for conventional processing to isolate the L-aspartic acid (acidification, precipitation, filtration, washing, recrystallization, drying).
 (ii) A continuous process wherein the catalyst compositions, e.g. coated beads, are placed in columns and the solutions of ammonium fumarate (concentrations, pH's, and tmeperatures are the same as described above for the batch processes) are passed through the catalyst beds either from above or from below (fluidized bed mode). The rates of passage of these fumarate solutions may range from 0.1 to 1000 space velocities/hour. For example, 5.0 liters of solution per hour may be passed through 0.1 liter of catalyst bed representing 5.0 space velocities (S.V.) per hour. Preferably the fumarate solution flow rates which yield essentially 100% conversion of the fumarate to the L-aspartate fall in the range of 0.5 to 20.0 S.V./hour. The effluent from these columns of catalyst beds is suitable for conventional processing to isolate L-aspartic acid (as outlined above in the batch processes).

As illustrative of processes which may be used to prepare L-phenylalanine according to the invention are the following:
 (i) A batch type process wherein the catalyst compositions are stirred in from 0.01 to 0.5 molar (preferably 0.05 to 0.3 molar) solution of phenylpyruvate in the presence of 0.015 to 0.75 molar ammonium L-aspartate (preferably 0.075 to 0.5 molar) and 0.4 to 0.000001 mmolar pyridoxal 5-phosphate (preferably 0.04 to 0.0004 mmolar in water at 5.0 to 10.0 pH (preferably 7.5 to 9.5 pH) for periods of 1.0 to 100 hours (preferably 8 to 48 hours) at temperatures below 50° C. (preferably 20° to 40° C.). Broadly from 0.05 to 50 g of immobilized cells, preferably from 1.0 to 15 g, are used per 0.1 mole of starting phenylpyruvate. After the conversion, the catalyst compositions may be removed by filtration or the equivalent for reuse in converting fresh batches of phenylpyruvate solutions. The product solutions are obtained in a form suitable for conventional processing to isolate the L-phenylalanine (ion exchange chromotography, precipitation, filtration, washing, recrystallization, drying).
 (ii) A continuous process wherein the catalyst compositions, e.g. coated beads, are placed in columns and the solutions of L-aspartate, phenylpyruvate and pyridoxal-5-phosphate (concentrations, pH's, and temperatures are the same as described above for the batch processes) are passed through the catalyst beds either from above or from below (fluidized bed mode). The rates of passage of these substrate solutions may range from 0.01 to 100 space velocities/hour. For example, 0.5 liters of solution per hour may be passed through 1.0 liter of catalyst bed representing 0.5 space velocities (S.V.) per hour. Preferably the phenylpyruvate/aspartate solution flow rates which yield essentially 100% conversion of the fumarate to the L-aspartate fall in the range of 0.05 to 0.5 S.V./hour. The effluent from these columns of catalyst beds is suitable for conventional processing to isolate L-phenylalanine (as outlined in the batch processes).

The invention is illustrated by the following examples:

EXAMPLE 1

Preparation of *E. coli* ATCC 11303 Immobilized in a gel of a polyfunctional aziridine (XAMA ®2). (PEI, N.B. #165, p. 78–79).

A well mixed slurry of 10.0 g of XAMA ®2 (Cordova Chemical of Michigan trimethylopropane-tris-[β-(N-aziridinyl)propionate]) and 10.0 g of *E. coli* ATCC 11303 (73% water) cell paste formed a solid, rubbery, water insoluble hydrogel within 11 minutes of mixing at 25° C. This gel composite was allowed to dry over 48 hours at 25° C. in air to form a hard, brittle resin-like solid. This solid was broken up into small particles (0.01–1.0 mm dia) by grinding in a Waring ® blender for 2 minutes. Particles passing through 25 mesh (U.S. std.) and retained on 35 mesh were used for activity experiment.

Approximately 3 g of the sieved particles were soaked in 25 ml of an aqueous solution, pH 8.5, of 0.1 molar Na phenylpyruvate, 0.15 molar ammonium aspartate plus 0.1 mmolar pyridoxal-5-phosphate for 24 hours at 25° C. (Sample #1a).

Another 3 g aliquot of the sieved particles was immersed in 25 ml of an aqueous solution, pH 8.8, containing 1.5 molar ammonium fumarate plus 1.0 m molar MgSO4 for 24 hours at 25° C. (sample #1b).

EXAMPLE 2

Preparation of *E. coli* ATCC 11303 Immobilized in a gel of a polyfunctional Aziridine (XAMA-7 ®). (PEI N.B. #165, p. 78–79).

In an identical process as described in Example 1, 10.0 g 2 XAMA-7 ® (Cordova Chem. Co. of Michigan, pentaerythritol-tris[β-(N-aziridinyl)propionate] and 10.0 g of *E. coli* ATCC 11303 cell paste was converted to a homogeneous hydrogel. As described in Example 1 the dried gel was broken up and sieved. As described in Example 1 portions of the sieved particles were either soaked in the NaPPA/NH4 L-ASP or NH4 fumarate solutions to give sample #2a and 2b respectively.

EXAMPLE 3

Preparation of high surface area resin beads coated with a gel of *E. coli* ATCC 11303 and polyfunctional aziridine (XAMA®2) (PEI N.B., #165, p. 80).

A homogeneous slurry of 50.0 g *E. coli* ATCC 11303 cell paste (73% H$_2$O) in 50.0 g of an aqueous solution containing 5.0 g of XAMA®2 (Cordova Chemical Company) was throughly mixed at 25° C. for 5 minutes (magnetic stirring bar in glass beaker). This slurry was blended with 50.0 g of anhydrous Amberlite® 938, (Rohm & Haas) large pore, ion exchange beads by thorough mixing at 25° C. for 15 minutes. The resultant wet, coated, free flowing beads weighed 151.25 g.

A 20.0 g aliquot of the damp, coated beads were allowed to dry in air at 25° C. for 24 hours, to give 9.2 g. dry, free flowing beads. A 4.6 g aliquot of these beads were immersed in 25 ml of an aqueous solution, pH 8.5, containing 0.1 molar sodium phenylpyruvate, 0.15 molar ammonium L-aspartate and 0.1 mmolar pyridoxal-5-phosphate for 24 hours at 25° C. (bead sample #3a). Another 4.6 g aliquot of the original 9.2 g dry beads was immersed in 25 ml aqueous solution of 1.5 molar ammonium fumarate plus 1.0 molar MgSO$_4$, pH 8.8, at 25° C. for 24 hours (bead sample #3b).

A 62.0 g. alquiot of the 151.25 g of damp, coated beads was allowed to cure by standing in a sealed container for 24 hours at 25° C. These cured coated beads were then immersed in an equal volume of an aqueous solution at 25° containing 0.1 molar sodium phenylpyruvate, 0.15 molar ammonium L-aspartate and 0.1 m molar pyridoxal-5-phosphate at pH 8.5 (bead sample #3c).

A 62.0 g aliquot of the 151.25 g damp, coated beads described in the first paragraph, Example 3, was allowed to cure by standing in a sealed container for 24 hours at 25° C. These cured, coated beads were then immersed in an equal volume of an aqueous solution at 25° C. containing 1.5 molar ammonium fumarate and 1.0 molar MgSO$_4$ at pH 8.5 (bead sample #3d).

EXAMPLE 4

Preparation of high surface area resin beads coated with a gel of *E. coli* ATCC 11303 and a polyfunctional Aziridine (XAMA®-7) (PEI, N.B., #165-p 80).

The procedure described in Example 4 was repeated using XAMA ®-7 in place of XAMA ®-P2 in the same proportions. The same results were obtained to give bead samnples 4a, 4b, 4c and 4d respectively.

EXAMPLE 5

L-PHE Production Activities of Material Prepared in Examples 1–4 (PEI, N.B. #165, p. 81, 83).

In all the following experiments in this example the materials were first washed with two or three times their volume of the above mentioned Na phenylpyruvate+NH$_4$-L-ASP+P-5-P solution just prior to the measurement of their activities. The L-PHE production rates in each case were measured by suspending 2.0 ml aliquots of the damp beads or particles in 25.0 ml of the aqueous solution, pH 8.5, containing 0.1 molar sodium phenylpyruvate, 0.15 molar ammonium L-aspartate and 0.1 m molar pyridoxal-5-phosphate. These slurries were gently stirred at 25° C. for periods of 23 hours. Samples of the clear supernatent reaction solutions were taken for L-phenylalanine content measurements by HPLC (C-18 Water Assoc.; 30% methanol in water containing 0.02 molar KN$_2$PO$_4$ run at 2.1 ml/min, 25° C.; samples diluted 50 μl/5 ml prior to injection; peak area at 3.90–3.95 minutes retention time represented L-PHE content compared to standard solutions of authentic L-PHE).

| Sample # | % PPA Converted to L-PHE in 23 hrs, 25° C. | moles L-PHE @ 25° C. hr × g cells |
|---|---|---|
| 1a (est. 0.64 g cells/2 ml) | 5.9 | 10.0 |
| 2a (est. 0.66 g cells/2 ml) | 6.6 | 10.9 |
| 3a (est. 0.53 g cells/2 ml) | 6.8 | 13.9 |
| 3c (est. .53 g cells/2 ml) | 2.3 | 4.7 |
| 4a (est. 0.58 g cells/2 ml) | 8.1 | 15.1 |
| 4c (est. 0.5 g cells/2 ml) | 6.1 | 11.4 |
| free cells *E. coli* ATCC 11303 (0.548 g) | | 50.9 |

Sample calculation:

$$4c \; \frac{0.475 \text{ peak area}}{0 - 774 \text{ std. peak area}} \times$$

$$\frac{0.01 \text{ m L-PHE in std.}}{0.1 \text{ m L-PHE theory completion}} \times 100 = 6.1\% \text{ conversion}$$

$$\frac{0.06 \text{ conversion} \times 0.1 \text{ moles theory completion}}{23 \text{ hrs} \times 0.58 \text{ g cells in 2 ml}} \times$$

$$\frac{25 \text{ ml sample}}{1000 \text{ ml/mole}} \times 10^6 = \frac{11.4 \; \mu \text{ moles L-PHE}}{\text{hr} \times \text{g cells}}$$

EXAMPLE 6

L-ASP Production Activities of Material Prepared in Examples 1–4 (PEI N.B. #165, p. 84,85).

In all of the following experiments in this example the materials were first washed with two to three times their volumes of the above described ammonium fumarate solution just prior to the measurement of their activities. The L-ASP production rates in each case were measured by the suspending 2.0 ml aliquots of the damp beads or particles in 25.0 ml of the aqueous solution, pH 8.8, containing 1.5 molar ammonium fumarate plus 1.0 mmolar MgSO$_4$ for periods of 1.0 hour at 25° C. Samples of the clear supernatant reaction solution were taken for L-aspartic acid content by measuring the disapearance of fumarate via loss in absorbence at 280 nm (samples first diluted 10 μl/10 ml H$_2$O) compared to standard solutions of authentic ammonium fumarate.

| Sample # | % NH$_4$ Fumarate concentrated L-ASP in in 1.0 hrs @ 25° C. | mmoles L-ASP @ 25° C. hr × g cells |
|---|---|---|
| 1b | 14.2 | 3.5 |
| 2b | 14.2 | 3.7 |
| 3b | 14.4 | 10.2 |
| 3d | 18.2 | 12.9 |
| 4b | 12.1 | 7.8 |
| 4d | 49.6 | 32.1 |
| free cells, *E. coli* ATCC 11303 (0.535 g) | | 36.4 |

Sample calculation:

$$4d \; 100 - \frac{(0.238 \; A_{280} \text{ mm sample})}{(0.472 \; A_{280} \text{ mm std.})} \times 100) = 49.6\%$$

$$\frac{0.496 \text{ conversion} \times 1.5 \text{ moles theory} \times 25 \text{ ml sample}}{1.0 \text{ hr} \times 0.58 \text{ g cells in 2 ml} \times 1000 \frac{\text{ml}}{\text{mole}}} =$$

$$\frac{0.032 \text{ moles L-ASP}}{\text{hr.} \times \text{g cells}}$$

EXAMPLE 7

Isolation of L-PHE Prepared by Cells Immobilized with Polyfunctional Aziridines and Measurement of Optical Purity (PEI N.B. #165, p 88).

A slurry of 75 ml wet coated beads prepared as described for sample #4C was rinsed with 75 ml of the previously described Na phenylpyruvate/NH4 L-ASP/P-5-P solution. The damp beads were then immersed in 150 ml of fresh 0.1 molar sodium phenylpyruvate, 0.15 molar ammonium aspartate, 0.1 mmolar pyridoxal-5-phosphate, pH 8.5, and gently stirred for 26 hours at 25° C.

The solids were then filtered from the reaction slurry. HPLC analysis of the clean, pale yellow, aqueous filtrate showed the presence of 0.18 molar L-PHE (9.51 g/150 ml). The solids were rinsed with 25 ml H2O two times. The combined filtrate and washings were adjusted to pH 2.0 with concentrated hydrochloric acid. The resultant slurry was concentrated to approximately 80 ml by evaporation at 85°–95° C. and 100 Torr. The pale yellow slurry was filtered free of solids at 25° C. The clear filtrate was adjusted to pH of 5.9 with concentrated ammonium hydroxide and then reduced in volume to 30 ml by evaporation at 85°–95° and 100 Torr. The resultant pale yellow slurry was heated to 100°–103° C. to bring all solids into solution and 60 to 70 ml of cold ispropanol were added to the unheated solution over a period of 3 to 4 minutes with good stirring. The resultant slurry was stirred at 25° C. for 3 hours. The resultant white crystalline solid was collected by filtration and recrystallized from 40 to 50 ml boiling water. The solids were collected by filtration and and rinsed with 10 ml cold water. After drying several days at 25° C. and 10 Torr there was obtained 2.4 g white crystals (53.3% yield of the available L-PHE).

A solution of 1.9 g of the white crystals in 100 ml H2O at 25° C. had an $[\alpha]_{Na}^{25°}$ C.$=-1.36$. An authentic sample of L-PHE measured under the same conditions had an $[\alpha]_{Na}^{25°}$ C.$=-1.35$.

EXAMPLE 8

Isolation of L-ASP Prepared by Cells Immobilized with Polyfunctional Azirdines and Measurement of Optical Purity (PEI N.B. 165, P. 87).

A slurry of 75 ml wet coated beads prepared as described for sample 4d was rinsed with 75 ml of the 1.5 molar ammonium fumarate/1.0 mmolar MgSO4 solution. The damp beads were then immersed in 150 ml of aqueous solution of 1.5 molar ammonium fumarate, 1.0 mmolar MgSO4, pH 8.8, for 26 hours at 25° C.

The solids were then filtered from the reaction slurry. U.V. analysis of the clear filtrate at 280 mm revealed more than 98% of the fumarate had been consumed. The solids were washed twice with 25 ml of water. The combined filtrate and washings were adjusted to pH 2.8 with concentrated hydrochloric acid. After stirring one hour at 25° C., the resultant slurry of white crystals was filtered. The wet cake of crystals was rinsed twice with 25 ml water. Upon drying several days at 25° C. and 10° Torr in air the white crystals weighed 25.5 g (estimate 85% yield of 30 g theory).

A solution of 2.0 g of the crystals in 100.0 ml 6N aqueous hydrochloric acid has an $[\alpha]_{Na}^{25°}$ C.$=+1.95$. An authentic sample of L-aspartic acid under the same condition had an $[\alpha]_{Na}^{25°}$ C.$=+1.97$.

What is claimed is:

1. A composition comprising immobilized cells having enzyme activity, the cells being immobilized by means of a fixed, insoluble, crosslinked polymer obtained by curing a curable polyfunctional aziridine prepolymer in admixture with said cells, said polymer being cured at a temperature below the temperature at which the enzyme activity of the microbial cells mixed therewith is significantly reduced.

2. A composition according to claim 1 coated on a solid inert carrier.

3. A composition according to claim 1 wherein the cells are whole cells of *E. Coli* which have L-aspartase or L-phenylalanine transaminase activity.

4. A composition according to claim 3 coated on a solid inert carrier.

5. A composition according to claim 1 wherein the cells are whole cells of *Pseudomonas dacunhae, Bacillus megaterium, Arthrobacter species, Arthrobacter simplex, Streptomyces phaeochromogenes* or *Rhodosporidium toruloides*.

6. A composition according to claim 2 or 4 wherein the carrier is a particulate support.

7. A composition according to claim 1 wherein the cells are *E. coli* cells having L-aspartase activity.

8. A composition according to claim 1 wherein the cells are *E. coli* cells having L-phenylalanine transaminase activity.

9. A process for preparing an immobilized microbial cell composition according to claim 1 which comprises mixing together an aqueous dispersion of the cells and prepolymer and curing the prepolymer in said mixture.

10. The process of claim 9 wherein the mixture is cured after application as a coating to a carrier.

11. The process of claim 10 wherein the coating is dried.

12. A process for preparing L-aspartic acid which comprises contacting ammonium fumarate with an immobilized microbial cell composition comprising cells containing L-aspartase activity immobilized by means of a fixed, insoluble crosslinked polymer obtained by curing a curable polyfunctional aziridine prepolymer in admixture with said cells, said polymer being cured at a temperature below the temperature at which the L-aspartase activity of the microbial cells is significantly reduced.

13. A process according to claim 12 wherein the cells are whole cells of *E. coli* 11303.

14. A process according to claim 12 wherein the immobilized microbial cell composition is coated on a solid inert carrier which comprises particulate material.

15. A process for preparing L-phenylalanine which comprises contacting a solution of phenylpyruvate salt with an immobilized microbial cell composition comprising cells containing L-phenylalanine transaminase activity immobilized by means of a fixed, insoluble crosslinked polymer obtained by curing a curable polyfunctional aziridine prepolymer in admixture with said cells, said polymer being cured at a temperature below the temperature at which the L-phenylalanine transaminase activity of the microbial cells is significantly reduced.

16. A process according to claim 16 wherein the immobilized microbial cell composition is coated on a carrier, which comprises particulate material.

17. A process for preparing L-alanine which comprises contacting L-aspartic acid solution with an immobilized microbial cell composition comprising cells containing L-aspartate decarboxylase activity immobilized by means of a fixed, insoluble crosslinked polymer obtained by curing a curale prepolymer of polyfunctional aziridine in admixture with said cells.

18. A process according to claim 17 wherein the immobilized microbial cell composition is coated on a carrier which comprises particulate material.

19. A process according to claim 17 wherein the cells are *Pseudomonas dacunhae* cells.

20. A process for preparing 6-Aminopencillanic acid which comprises using an immobilized microbial cell composition comprising cells containing penicillin-G acylase activity immobilized by means of a fixed, insoluble, crosslinked polymer obtained by curing a curable prepolymer of polyfunctional aziridine in admixture with said cells.

21. A process according to claim 20 wherein the immobilized microbial cell composition is coated on a carrier which comprises particulate material.

22. A process for producing high fructose corn syrup which comprises using an immobilized microbial cell composition comprising cells containing glucose isomerase activity immobilized by means of a fixed, insoluble, crosslinked polymer obtained by curing a curable prepolymer of polyfunctional aziridine in admixture with said cells.

23. A process according to claim 22 wherein the immobilized microbial cell composition is coated on a carrier which comprises particulate material.

24. A process for producing steroids which comprises using an immobilized microbial cell composition comprising cells having steroid dehydrogenase activity immobilized by means of a fixed, insoluble, crosslinked polymer obtained by curing a curable prepolymer of polyfunctional aziridine in admixture with said cells.

25. A process according to claim 24 wherein the immobilized microbial cell composition is coated on a carrier which comprises particulate material.

26. A process for producing phenylalanine which comprises using an immobilized microbial cell composition comprising cells containing phenylalanine ammonia-lyase activity immobilized by means of a fixed, insoluble, crosslinked polymer-obtained by curing a curable prepolymer of polyfunctional aziridine in admixture with said cells.

27. A process according to claim 26 wherein the immobilized microbial cell composition is coated on a carrier which comprises particulate material.

* * * * *